(12) United States Patent
Bridges

(10) Patent No.: US 11,642,082 B1
(45) Date of Patent: May 9, 2023

(54) METHOD AND APPARATUS FOR SENSOR ADHESIVE LIFE EXTENSION

(71) Applicant: Timothy Bridges, Huntington Beach, CA (US)

(72) Inventor: Timothy Bridges, Huntington Beach, CA (US)

(73) Assignee: Timothy E. Bridges

( * ) Notice: Subject to any disclaimer, the term of this patent is extended or adjusted under 35 U.S.C. 154(b) by 291 days.

(21) Appl. No.: 17/122,408

(22) Filed: Dec. 15, 2020

Related U.S. Application Data

(60) Provisional application No. 62/952,190, filed on Dec. 20, 2019.

(51) Int. Cl.
*A61B 5/00* (2006.01)
*A61B 5/145* (2006.01)

(52) U.S. Cl.
CPC ........ *A61B 5/6833* (2013.01); *A61B 5/14532* (2013.01); *A61B 5/6831* (2013.01)

(58) Field of Classification Search
CPC .. A61B 5/6833; A61B 5/14532; A61B 5/6831
See application file for complete search history.

(56) References Cited

U.S. PATENT DOCUMENTS

| | | | | |
|---|---|---|---|---|
| 5,050,612 A | * | 9/1991 | Matsumura | A61B 5/14532 374/E13.002 |
| 5,938,619 A | * | 8/1999 | Dogre Cuevas | A61B 5/0008 600/549 |
| 6,085,449 A | * | 7/2000 | Tsui | A45C 13/42 224/267 |
| 6,238,354 B1 | * | 5/2001 | Alvarez | G01K 1/024 374/E1.004 |
| 2014/0296756 A1 | * | 10/2014 | Ganske | A61B 5/02233 601/151 |
| 2014/0365946 A1 | * | 12/2014 | Sankaralingham | G06F 1/163 715/773 |
| 2016/0171417 A1 | * | 6/2016 | Sankaralingham | G06F 3/04886 705/7.42 |
| 2017/0340210 A1 | * | 11/2017 | Chuang | A61B 5/02141 |
| 2022/0087575 A1 | * | 3/2022 | Persidsky | G16H 40/63 |

* cited by examiner

Primary Examiner — Steven O Douglas

(57) ABSTRACT

A method and apparatus for extending the life of a continuous glucose monitor adhesive sensor patch on the body. The apparatus includes an adhesive hold-down, an elastic fabric, and adhering attachments such as Velcro. The apparatus can be fitted around a user's body, with the adhesive hold-down positioned over the sensor adhesive. The apparatus then protects the adhesive from peeling away from skin while in the shower, swimming, or other activities that deteriorate the adhesive.

3 Claims, 3 Drawing Sheets

METHOD AND APPARATUS FOR SENSOR ADHESIVE LIFE EXTENSION

CROSS-REFERENCE TO RELATED APPLICATION

This application claims the benefit of the filing date of the Provisional Application Ser. No. 62/952,190, filed on Dec. 20, 2019, which is incorporated herein by reference.

FIELD

The present disclosure relates generally to wearable systems and, in particular, to a method and apparatus for extending the useful life of a continuous glucose monitor sensor's adhesive patch that affixes a sensor to a person's skin.

BACKGROUND

There are electronic sensors and other devices which affix to a person's skin with adhesive patches that are part of the sensor system. These adhesive patches typically last 7 to 14 days. The life of the adhesive patch is diminished by deterioration from skin perspiration under and around the patch, by water flowing over the edges of the adhesive patch while showering or swimming, and by other physical activities. As adhesive patch life shortens, the sensor or other device may prematurely dislodge or otherwise discontinue expected functions. Sensors can be very expensive, so any shortening of adhesive life may require the sensor to be replaced earlier than intended, driving addition cost to the user. An illustration of adhesive degradation and detachment from the skin, diminishing adhesive patch life is shown in FIG. 2A.

Larger adhesive over-patches may be placed over the sensor patch to extend life, but the large adhesive area may cause an adverse skin reaction due to the chemicals. Further, it must be affixed for the duration of the sensor, continuously presenting additional size, which may appear unsightly. Medical tape may also be applied at the edges of the adhesive patch, but these tapes are awkward to cut and place, and often cause adverse skin reactions. Although these adhesive based measures may be useful, their appearance, awkwardness, and adverse skin reactions make them inconvenient for some users. A low-cost simple means of extending the life of a sensor's original adhesive patch would be beneficial.

SUMMARY

The sensor adhesive life extension method and apparatus provides a simple mechanical protection of the adhesive patch while the user is showering, swimming, or performing other temporary activities that deteriorate the adhesive. Showering, for example, dominates the several causes of sensor adhesive deterioration. Neutralizing the dominating cause of adhesive deterioration would extend the useful life of the adhesive patch. A user would simply place the apparatus around their body, positioning the adhesive hold-down over the adhesive patch. Once the patch is covered and lightly pressed against the skin, shower water will no longer peel away the patch, thereby extending adhesive life. This apparatus is useful when larger covering adhesive patches or medical tape are unsightly or cause the user skin irritation.

BRIEF DESCRIPTION OF THE DRAWINGS

The present invention will become more fully understood from the detailed descriptions and the accompanying drawings, wherein:

FIG. 2A illustrates adhesive degradation and detachment from the skin. FIG. 2B illustrates donning the apparatus of the present invention by placing it around the body using elastic body straps 3 and 4. FIG. 2C illustrates positioning the adhesive hold-down 2 over the sensor patch.

DETAILED DESCRIPTION

Figure 1A:
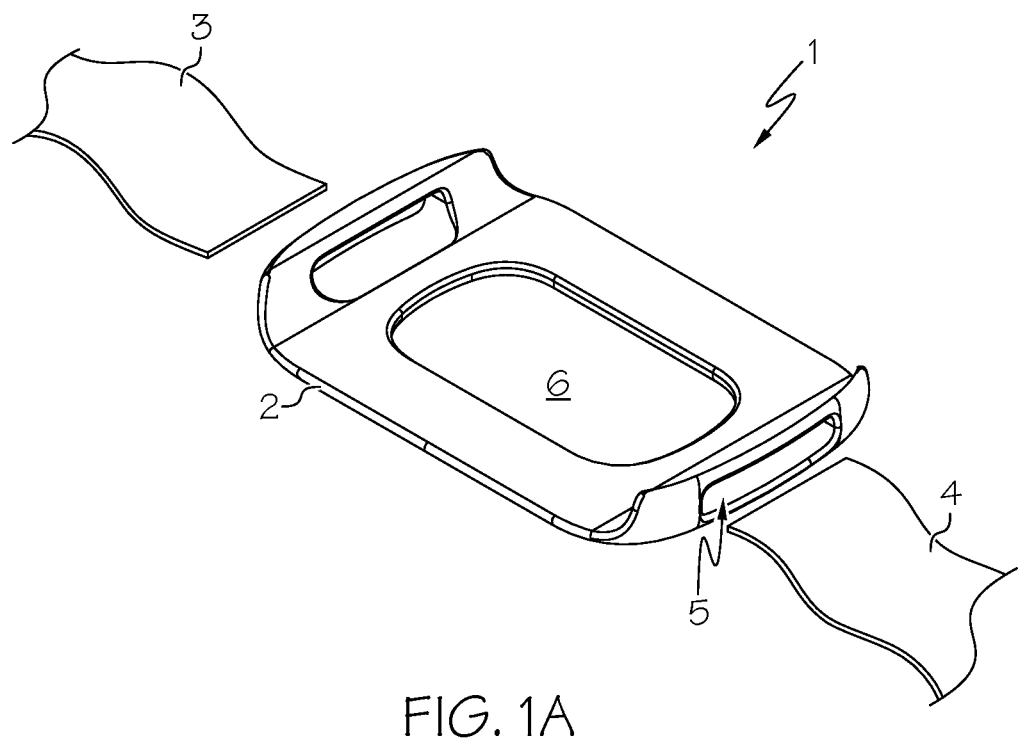
FIG. 1A is an isometric illustration of the adhesive hold-down, along with straps that comprise the apparatus of the present invention.
Figure 1B:
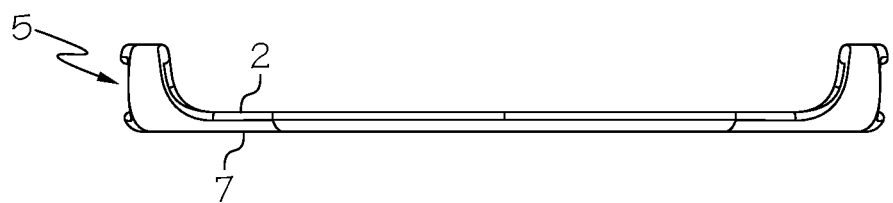
FIG. 1B provides a front view of the adhesive hold-down.

Described herein is an adhesive life extension apparatus 1, as depicted in FIG. 1A. The adhesive life extension apparatus 1 includes an adhesive hold-down 2, and elastic body strap long 3, and elastic body strap short 4. The elastic body straps 3 and 4 attach to the adhesive hold-down 2 via the end slots 5. The loose ends of body straps 3 and 4 incorporate an adhering material such as Velcro so they may be attached to each other, holding the apparatus 1 in place. The body strap long 4 wraps around the majority a user's body, allowing him or her to attach the Velcro loop end to body strap short 3 Velcro hook end with hands located near adhesive hold-down 2.

Figure 2A:
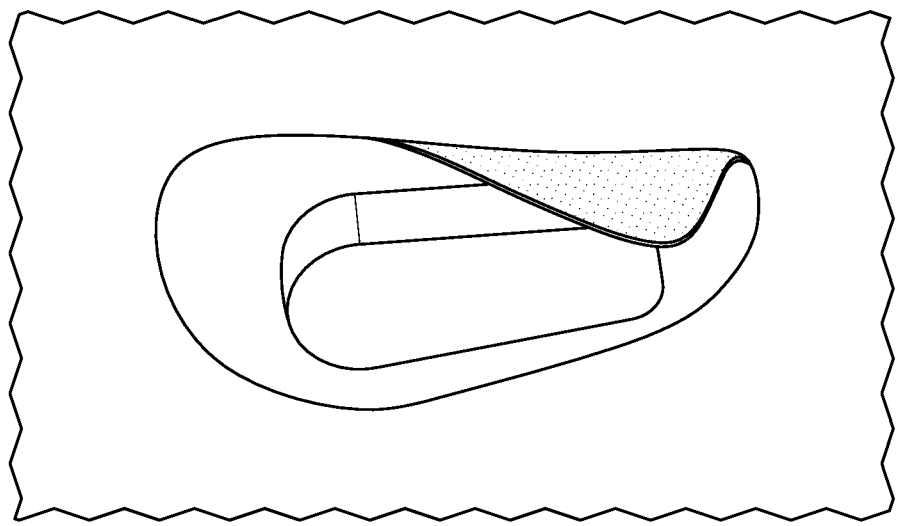
FIGS. 2A through 2C illustrates the operation of the present invention by detailing the problem being addressed and the useful benefit.
Figure 2B:
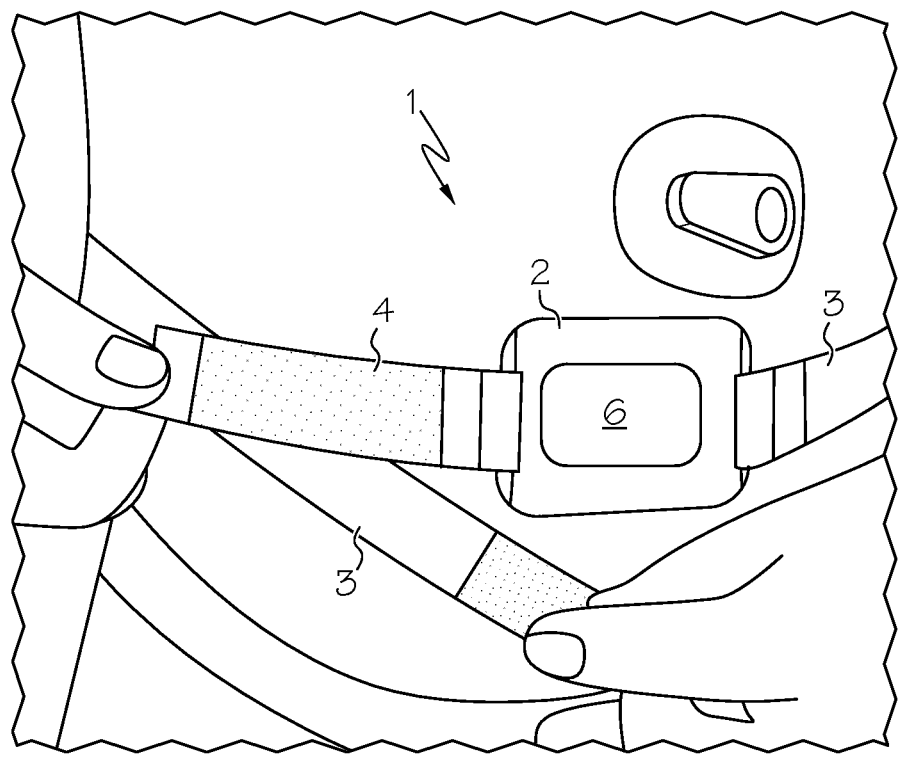

The adhesive hold-down 2 is configured symmetrically to accommodate right and left-handed users equally. The apparatus is thereby wearable with body strap long 3, and body strap short 4, on either the right or left, to accommodate right-handed and left-handed operation. A right-handed user donning on the apparatus is depicted in FIG. 2B.

End slots 5 are configured to impart a nominal downward pressure against a user's skin via hold-down body surface 7 when elastic body straps 3 and 4 are worn around the body. Further, end slots 5 are configured to ensure pressure is nominal and does not impact to sensor function. In the present embodiment, the end slots 5 are located longitudinally on the adhesive hold-down 2 in order to accommodate a user's adhesive patch that is aligned across the body as in FIG. 2C. Other embodiments may place the end slots 5 clocked 90 degrees around adhesive hold-down 2, allowing the hold-down to orient vertically on a user for vertically oriented sensors The adhesive hold-down 2 incorporates a hold-down center hole 6 to ensure sensor operation is not impacted. The hold-down center hole 6 is configured to accommodate a sensor whose longitudinal axis is different than the longitudinal axis of the hold down 2, in the plane of the user's skin. This allows variability in the user's longitudinal alignment of his or her sensor, while still covering the adhesive patch, and can be seen in FIG. 2C. Further, the hold-down center hole 6 is configured with curved edges and rounded surfaces to minimize edges catching on a user's sensor while donning and doffing the apparatus.

Figure 2C:
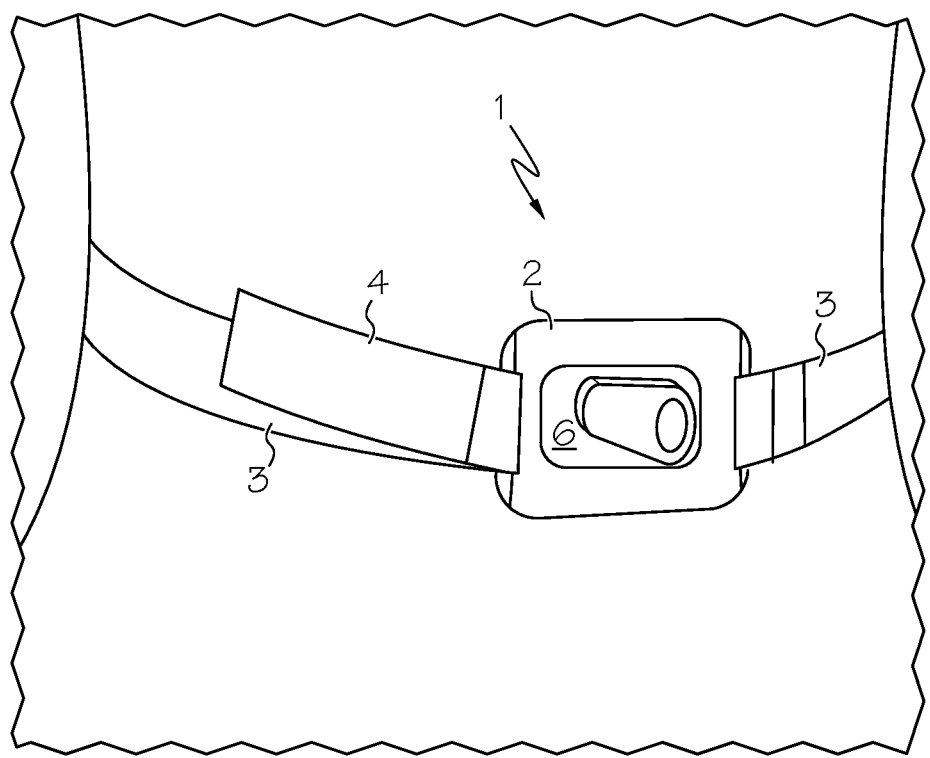

The invention's operation is illustrated by the following figures. FIG. 2A shows sensor adhesive deterioration and the associated peeling away from the skin. As peeling away occurs, shower water running down the body causes further deterioration of the sensor patch adhesive. This deleterious effect can be neutralized by the present invention as shown in FIG. 2B and FIG. 2C. FIG. 2B shows a user donning the adhesive life extension apparatus 1, by wrapping the elastic straps 3 and 4 around the body and attaching them with an adhering material such as Velcro as described in the above paragraphs. FIG. 2C shows the user has adjusted the placement of the adhesive hold-down 2 over the sensor patch. Thus the apparatus covers the edge of the adhesive, neutralizing the deleterious effect of shower water, thereby extending the adhesive's useful life.

The invention has been described for the purposes of illustration and description, and is not intended to be exhaustive or limited to the embodiments in the form disclosed. Modifications and variations will be apparent to those of ordinary skill in the art. The embodiment selected is chosen and described in order to best explain the principles of the invention and the practical application, and to enable others of ordinary skill in the art to understand the disclosure as it may apply to any particular use contemplated.

What is claimed is:

1. An apparatus for extending the adhesive life of a continuous glucose monitor sensor patch, the apparatus comprising:

a symmetric adhesive patch hold-down plate with a center hole to ensure contact with a sensor's adhesive patch while avoiding contact with the continuous glucose monitor sensor itself;

end slots of said hold-down plate wherein said end slots extend away from a person's skin for ensuring downward pressure against a person's skin when receiving two elastic body straps; and a long and a short elastic strap wherein each is attached to a different hold-down plate end slot, with adhering material on non-attached strap ends such that a person can use the straps to secure the hold-down plate to their body.

2. The apparatus of claim 1, wherein the adhesive hold-down plate is configured to extend past the edges of the adhesive patch to reduce the effect of shower water degradation of adhesive.

3. The apparatus of claim 2, wherein the adhesive life extending apparatus is symmetrically configured to operate by left or right-handed users.

* * * * *